United States Patent [19]

Fehr et al.

[11] 4,076,715
[45] Feb. 28, 1978

[54] 13-BROMO LYSERGIC ACID COMPOUNDS

[75] Inventors: Theodor Fehr, Dornach; Hartmut Hauth, Riehen, both of Switzerland

[73] Assignee: Sandoz Ltd., Basel, Switzerland

[21] Appl. No.: 580,362

[22] Filed: May 23, 1975

Related U.S. Application Data

[62] Division of Ser. No. 399,167, Sep. 20, 1973, Pat. No. 3,901,891.

[30] Foreign Application Priority Data

Sep. 26, 1972  Switzerland ..................... 14032/72
Sep. 26, 1972  Switzerland ..................... 14033/72

[51] Int. Cl.$^2$ .................... C07D 457/04; A61K 31/48
[52] U.S. Cl. .......................... 260/285.5; 260/268 PE; 260/268 TR; 424/261; 424/250
[58] Field of Search ..................................... 260/285.5

[56] References Cited

U.S. PATENT DOCUMENTS 3,904,634  9/1975  Arcari et al. ..................... 260/285.5

Primary Examiner—Donald G. Daus
Assistant Examiner—Mary Vaughn
Attorney, Agent, or Firm—Gerald D. Sharkin; Robert S. Honor; Thomas O. McGovern

[57] ABSTRACT

The present invention concerns novel 13-bromo-lysergic acid compounds of formula I:

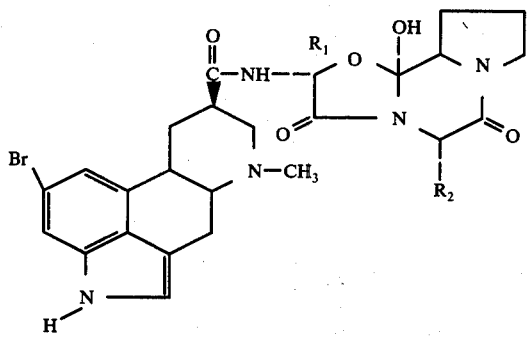

wherein
  $R_2$ is isopropyl, 1 or 2-methylpropyl or benzyl, useful as agents for the treatment of cerebral insufficiency.

6 Claims, No Drawings

13-BROMO LYSERGIC ACID COMPOUNDS

This is a division of copending application, Ser. No. 399,167, filed Sept. 20, 1973, now U.S. Pat. No. 3,901,891, the contents of which are incorporated herein by reference.

The present invention relates to novel 13-bromolysergic acid compounds.

The present invention provides compounds of formula I,

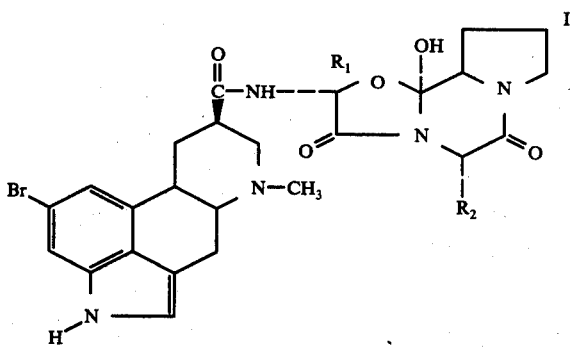

wherein
$R_1$ is methyl or iospropyl, and
$R_2$ is isopropyl, 1-methylpropyl, 2-methylpropyl or benzyl.

Further, in accordance with the invention, a compound of formula I may be obtained by a process comprising reacting a reactive, functional acid derivative of an acid of formula II,

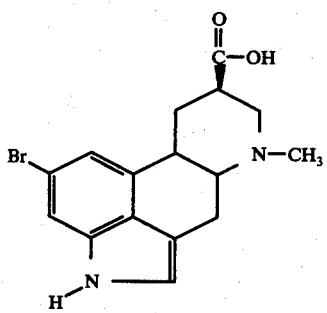

with an acid addition salt of a compound of formula III,

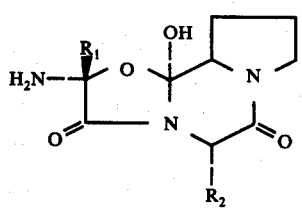

wherein $R_1$ and $R_2$ are as defined above,
in an inert solvent or solvent mixture, in the presence of a basic condensation agent.

The reaction may be conveniently effected in conventional manner.

In accordance with a preferred method for effecting the process of the invention, the reaction product obtained from reaction of the acid of formula II, i.e. of 13-bromo-9,10-dihydro-lysergic acid, with a chlorinating agent, e.g. oxalyl chloride, thionyl chloride, phosgene or phosphorus oxychloride, and an N-di(lower)alkyl-substituted acid amide of an aliphatic monocarboxylic acid having 1 to 3 carbon atoms, the N-alkyl substituents independently having from 1 to 3 carbon atoms, such as dimethyl formamide or dimethyl acetamide, is used as reactive derivative of the acid of formula II.

In accordance with a further preferred method of effecting the process, the mixed anhydride obtained from reaction of the acid of formula II with trifluoroacetic acid anhydride is used.

Alternatively, other suitable reactive derivatives of the acid of formula II may be used, e.g. the acid chloride hydrochloride, the acid azide, the addition product of the acid of formula II with carbodiimide, or mixed anhydrides of the acid of formula II with other acids, e.g. sulphuric acid.

The reaction with an acid addition salt of a compound of formula III may be effected at a temperature from about −30° to about 0° C. Examples of inert organic solvents which may be used for the reaction are aprotic solvents such as acetonitrile, chloroform, methylene chloride, dimethyl formamide or mixtures thereof. Examples of basic condensation agents suitable for use in the reaction are tertiary amines such as pyridine.

The reaction is, for example, effected by adding the acid of formula II at −30° C to a suspension of oxalyl chloride and dimethyl formamide in an inert organic solvent, preferably acetonitrile. The order of addition of the above-mentioned reagents may be varied if desired. Stirring may be effected conveniently at 0° C. The hydrochloride salt form of a compound of formula III may be added to the reaction mixture conveniently at −30° C with addition of a tertiary organic base, e.g. pyridine. Warming is then effected to bring the mixture to 0° C and stirring is effected for about two hours.

Working up may be effected by pouring the reaction mixture on ice and extracting with methylene chloride. The compounds of formula I are isolated in known manner from the organic phase and conveniently isolated acid addition salt form.

Alternatively, trifluoroacetic acid anhydride may be added conveniently at −20° C to a suspension of the acid of formula II in an inert organic solvent, preferably acetonitrile. After the mixture is stirred at −20° C, the resulting mixed anhydride may be reacted in the presence of a tertiary organic base, e.g. pyridine, with an acid addition salt of a compound of formula III, dissolved in trifluoroacetic acid. The reaction mixture may be worked up in known manner.

The present invention also provides 13-bromo-9,10-dihydro-lysergic acid used as starting material in the above process which acid may be obtained by a process comprising a. brominating 9,10-dihydro-lysergic acid of formula IV,

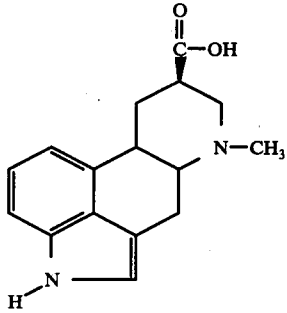

to produce a compound of formula V,

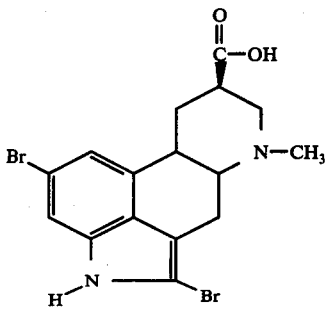

and selectively debrominating the compound of formula V to produce 13-bromo-9,10-dihydro-lysergic acid, or b. brominating a compound of formula VI,

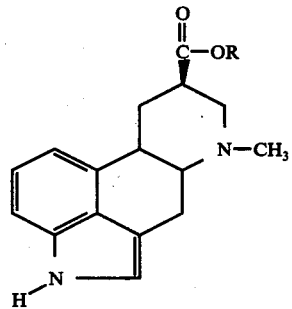

wherein R is alkyl of 1 to 6 carbon atoms, to produce a compound of formula VII,

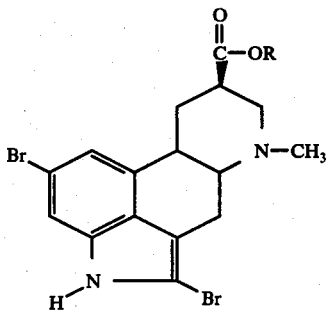

wherein R is as defined above, and selectively debrominating the compound of formula VII to produce a compound of formula VIII,

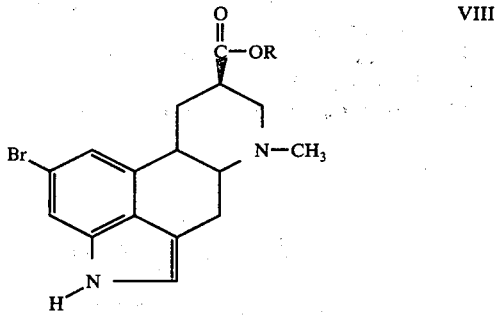

wherein R is as defined above, and hydrolysing the compound of formula VIII to produce 13-bromo-9,10-dihydro-lysergic acid.

The bromination of process variant (a) is preferably effected in an organic solvent such as an acid, for example glacial acetic acid or propionic acid. The reaction is preferably effected at a temperature from 10° to 80° C. Preferred brominating agents contain elementary bromine, for example pyridine hydrobromide perbromide.

The selective debromination of process variant (a) may be effected reductively, e.g. by catalytic hydrogenation or by zinc dust reduction.

Catalytic hydrogenation is conveniently effected at room temperature. Raney nickel is a suitable catalyst. The hydrogenation must be stopped after the uptake of one equivalent of hydrogen. 13-Bromo-9,10-dihydro-lysergic acid of formula II may be isolated from the filtrate in known manner.

The zinc dust reduction is preferably effected in glacial acetic acid. After the addition of the zinc dust preferably in the presence of hydrochloric acid, the reaction mixture may be heated preferably to about 80° C.

The bromination of process variant (b) is conveniently effected in an organic solvent such as an acid, e.g. glacial acetic acid or propionic acid. The reaction is conveniently effected at a temperature of from 10° to 80° C. The reaction may be effected with a brominating agent containing elementary bromine, preferably pyridine hydrobromide perbromide.

The debromination of process variant (b) may be carried out reductively, preferably with zinc dust in hydrochloric acid. The reaction is conveniently effected at an elevated temperature, preferably at about 80° C. The reaction may conveniently be effected in an acid solvent such as glacial acetic acid.

The hydrolysis of process variant (b) may be carried out in conventional manner, conveniently in the presence of a base, for example sodium hydroxide. The reaction is conveniently effected in methanol.

The above-mentioned acids may be converted into salt form and ester form in conventional manner and vice versa.

Insofar as the production of the starting materials is not particularly described, these compounds are known or may be produced and purified in accordance with known processes or in a manner analogous to processes described herein or known processes.

Free base forms of the compounds of formula I are usually crystalline at room temperature. Free base forms of compounds of formula I may be converted into acid addition salt forms in conventional manner, and vice versa.

Representative acids for acid addition salt formation include the organic acids such as tartaric acid, fumaric acid, oxalic acid, and maleic acid and the mineral acids such as the hydrohalide acids.

The compounds of formula I have not been described in the literature.

The compounds of formula I are useful because they possess pharmacological activity in animals. In particular, the compounds of formula I are useful as agents for the treatment of cerebral insufficiency in animals as indicated by an increase in vigilance indicated in the following standard tests in animals, by:

i. A prolongation of the waking phase, a shortening of the classical sleep phases, a shortening of the paradoxical sleep phases and a prolongation of the latency period till the onset of first paradoxical sleep, as determined by E.E.G. measurements in the non-narcotized rat on i.p. administration of from 3 to 10 mg per kilogram animal body weight, of the compounds.

ii. A reduction in the number of P.G.O. spikes in the "Corpus geniculatum laterale" induced by reserpine in cats on i.v. administration of from 0.1 to 0.5 mg per kilogram animal body weight, of the compounds, and iii. An antagonism of the E.E.G. changes relating to $\alpha$, $\beta$ and $\Delta$ waves induced by ischemia in the perfused cat head on administration of from 100–500 mg, of the compounds, wherein similar effects are obtained to the known ceberal insufficiency agent HYDERGIN (Registered Trade Mark).

For the above mentioned use the dosage will, of course, vary depending on the compound employed, mode of administration and therapy desired. However, in general, satisfactory results are obtained when administered at a daily dosage of from 0.1 mg to about 10 mg per kg animal body weight, conveniently given in divided doses 2 to 4 times a day or in sustained release form. For the larger mammal, the total daily dosage is in the range from about 5 to about 60 mg, and dosage forms suitable for oral administration comprise from about 1 mg to about 30 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acids for acid addition salt formation include organic acid salt forms such as the tartaric, fumaric, oxalic and maleic acids and methane sulphonate and mineral acids such as the hydrochloric, hydrobromic and sulphuric acids. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

In a preferred group of compounds $R_2$ is isobutyl (2-methylpropyl), or especially isopropyl (1-methylethyl) or benzyl.

In the following non-limitative Examples all temperatures are indicated in degrees Centigrade. Room temperature is from 15° to 30° C. A suitable vacuum is between 8 and 20 nm Mercury unless otherwise stated.

EXAMPLE 1

13-bromo-9,10-dihydro-ergotamine

A solution of 3.01 cc (35 millimols) of oxalyl chloride in 50 cc of absolute acetonitrile is added dropwise at −30° within 5 minutes, while stirring, to 70 cc of absolute dimethyl formamide and 140 cc of absolute acetonitrile, and the crystalline mash is stirred at −30° for a further 5 minutes. 12.25 g (35 millimols) of anhydrous 13-bromo-9,10-dihydrolysergic acid are subsequently added, the suspension is stirred at 0° for 30 minutes, is cooled to −30° and 24.5 cc of pyridine and 5.85 g (17.5 millimols) of (2R,5S,10aS,10bS)-2-methyl-2-amino-5-benzyl-3,6-dioxo-10b-hydroxy-octahydro-8H-oxazolo[3,2-a]pyrrolo[2,1-c]pyrazine hydrochloride are successively added. After stirring at 0° for 2 hours, the reaction mixture is poured onto ice, extracted with methylene chloride, and the methylene chloride phases are successively washed with a 10% soda solution and water, dried and concentrated by evaporation. The residue is crystallized from acetone/ether. The title compound is obtained in the form of colourless crystals having a M.P. of 248–250° (decomp.); $[\alpha]_D^{21} = -53°$ (c = 0.5; pyridine).

EXAMPLE 2

13-bromo-9,10-dihydro-ergotamine 1.58 cc (10.5 millimols) of trifluoroacetic acid anhydride are added at −20° within 10 minutes to a suspension of 3.5 g (10 millimols) of anhydrous 13-bromo-9,10-dihydro-lysergic acid in 100 cc of absolute acetonitrile, in the absence of moisture while a stream of nitrogen is passed through. After stirring at −20° for 30 minutes, 2.23 g of (2R, 5S, 10aS, 10bS)-2-methyl-2-amino-5-benzyl-3,6-dioxo-10b-hydroxy-octahydro-8H-oxazolo[3,2-a]pyrrolo[2,1-c]pyrazine hydrochloride, dissolved in 7 cc of trifluoroacetic acid, and 13.5 cc of pyridine are rapidly and successively added to the yellow solution. The reaction mixture is stirred at −20° for 1 hour, 13.5 cc of water are subsequently added, concentration is effected at 30°, the residue is taken up in methylene chloride, is washed with a 10% soda solution and water, dried and concentrated by evaporation. Crystallization from acetone/other yields the title compound as colourless crystals having a M.P. of 248–250° (decomp.); $[\alpha]_D^{21} = -53° \pm 2°$ (c = 0.5; pyridine).

Hydrogen Tartrate

The base is dissolved in acetone, the calculated amount of tartaric acid is added and crystallization is effected. The hydrogen tartrate, having a M.P. of 208°–210° (decomp.), is obtained; $[\alpha]_D^{21} = +19°$ (c = 0.5; ethanol/water 1:1).

(Hydrochloride
From acetone/ether, M.P. 217°–218°, $[\alpha]_D^{21} = 19.5°$ (c = 0.40 in 50% ethanol).

Hydrogen Fumarate

From acetone/ether, M.P. 198°–200°, $[\alpha]_D^{21} = +16°$ (c = 0.51 in 50% ethanol).

EXAMPLE 3

13-bromo-9,10-dihydro-ergocristine 10.5 g (30 millimols) of anhydrous 13-bromo-9,10-dihydro-lysergic acid in 300 cc of absolute acetonitrile are reacted in a manner analogous to that described in Example 2, with 4.74 cc (31.5 mols) of trifluoroacetic acid anhydride, 7.92 g (20 millimols) of (2R,5S,10aS,10bS)-2-isopropyl-2-amino-5-benzyl-3,6-dioxo-10b-hydroxy-octahydro-8H-oxazolo[3,2-a]pyrrolo[2,1-c]pyrazine hydrochloride, dissolved in 21 cc of trifluoroacetic acid, and 40.5 cc of pyridine. Crystallization of the residue from acetone/ether after working up yields the title compound as colourless crystals having a M.P. of 209°–211°; $[\alpha]_D^{21} = -43°$ (c = 0.5; pyridine).

Hydrogen Maleate

The base is dissolved in acetone, the calculated amount of maleic acid is added and crystallization is effected. Colourless crystals having a M.P. of 196°–198°, are obtained; $[\alpha]_D^{21} = +18°$ (c = 0.5; ethanol/water 1:1).

EXAMPLE 4

13-bromo-9,10-dihydro-ergocornine

The reaction is effected in a manner analogous to that described in Example 2, with (2R,5S,10aS,10bS)-2,5-diisopropyl-2amino-3,6-dioxo-10b-hydroxy-octahydro-8H-oxazolo[3,2-a]pyrrolo[2,1-c]pyrazine hydrochloride. The base is thin layer chromatographically and spectrographically uniform.

The base is dissolved in acetone and, the calculated amount of 3 N hydrochloric acid in ether is added. The hydrochloride of the title compound is obtained in the form of colourless crystals having a M.P. of 218°–220° (decomp.); $[\alpha]_D^{21} = +36°$ (c = 0.5; ethanol/water 1:1).

EXAMPLE 5

13-bromo-9,10-dihydro-β-ergocryptine

The reaction is effected in a manner analogous to that described in Example 1, with (2R,5S,10aS,10bS)-2-isopropyl-2-amino-5-(1-methylpropyl)dioxo-10b-hydroxy-octahydro-8H-oxazolo[3,2-a]pyrrolo[2,1-c]pyrazine hydrochloride. The resulting title compound crystallizes from methylene chloride/ether, M.P. 190°–192° (decomp.); $[\alpha]_D^{21} = -12°$ (c = 0.5; pyridine).

Hydrogen Oxalate

The base is dissolved in methanol, the calculated amount of oxalic acid is added and crystallization is effected; M.P. 192°–194° (decomp.); $[\alpha]_D^{21} = +41°$ (c = 0.5; ethanol/water 1:1). 13-Bromo-9,10-dihydro-α-ergocryptine is obtained in analogous manner.

The 13-bromo-9,10-dihydro-lysergic acid, used as starting material, may be obtained in accordance with the following methods A and B:

METHOD A a. 2,13-dibromo-9,10-dihydro-lysergic acid 40.5 g of 9,10-dihydrolysergic acid are dissolved in 1.15 liters of glacial acetic acid while heating slightly, the red-brown solution is cooled to 10°, 104.9 g of pyridine hydrobromide perbromide are added and stirring is subsequently effected at room temperature. After 2 hours, the reaction mixture is concentrated to half its volume in a vacuum, the residue is rendered alkaline with concentrated ammonia while cooling with ice and the resulting light brown precipitate is filtered off. Further purification is effected by dissolving the moist filter residue in 300 cc of concentrated ammonia and 300 cc of methanol while heating, adding active charcoal, filtering and concentrating in a vacuum until crystallization commences. After allowing to stand overnight at 0°, filtration is effected, washing is effected with a small amount of methanol and drying is effected in a vacuum at 80°. Light yellow crystals, having a M.P. from 290° (decomp.), are obtained; $[\alpha]_D^{20} = -91° \pm 3°$ (c = 0.5 in pyridine).

b. 13-bromo-9,10-dihydro-lysergic acid

A solution of 2.2 g (5 millimols) of 2,13-dibromo-9,10-dihydro-lysergic acid in 10 cc of triethylamine and 50 cc of water is hydrogenated at room temperature with the addition of 2.2 g of moist Raney nickel. After the take up of one equivalent of $H_2$, hydrogenation is stopped, the catalyst is filtered off and the filtrate is acidified with 2N hydrochloric acid while cooling with ice (pH 4.5–5.0). The resulting precipitate is filtered off, is dried in a vacuum over phosphorus pentoxide and recrystallized from methanol/methylene chloride/concentrated ammonia. The title compound is obtained as colourless needles, decomp. from 290°, $[\alpha]_D^{21} = -57°$ (c = 0.5 in pyridine).

c. 13-bromo-9,10-dihydro-lysergic acid 5 g of 2,13-dibromo-9,10-dihydro-lysergic acid are suspended in 75 cc of glacial acetic acid, and 30 cc of 2N hydrochloric acid and 30 g of zinc dust are added. The reaction mixture is heated to 80°, is filtered whilst hot after 4 hours and the filter residue is washed with 25 cc of 50% acetic acid. The filtrate is concentrated in a vacuum, Methanol is added to the residue and the resulting mixture concentrated again in a vacuum. The methanol addition and concentration is repeated twice. The resulting residue is again dissolved in 30 cc of methanol, and a 2N caustic soda solution is added while heating until an alkaline reaction (pH 12) is obtained. The resulting precipitate is filtered off and the acid product is precipitated by the addition of glacial acetic acid until a pH of 4.6 is obtained. The crystalline acid product which has been filtered off is washed with water, methanol and acetone. Recrystallization is effected by dissolving in methanol saturated with ammonia, and concentrating carefully in a vacuum until crystallization commences, whereby 13-bromo-9,10-dihydro-lysergic acid is obtained with the characteristics indicated in section (b) above.

METHOD B a. 2,13-dibromo-9,10-dihydro-lysergic acid methyl ester 56 g (200 millimols) of 9,10-dihydro-lysergic acid methyl ester are dissolved in 1000 cc of glacial acetic acid, and 146 g (440 millimols) of pyridine hydrobromide perbromide are added at room temperature. A light green precipitate is formed which is filtered off after a reaction time of two hours. After washing with methanol, the filter residue is partitioned between methylene chloride and a 20% potassium bicarbonate solution. The organic phase is dried over sodium sulphate and evaporated to dryness in a vacuum. The title compound crystallizes from methanol, M.P. 264°–265° (decomp.); $[\alpha]_D^{20} = -56.8°$ (c = 0.578 in methylene chloride).

b. 13-bromo-9-10-dihydro-lysergic acid methyl ester 22 g (49.8 millimols) of 2,13-dibromo-9,10-dihydrolysergic acid methyl ester are dissolved in 300 cc of glacial acetic acid, and 120 cc of 2N hydrochloric acid and 120 g of zinc dust are added. Heating to 80° is effected for 15 hours while stirring. Working up is effected by filtering off the excess zinc and washing the residue with water and concentrated ammonia. The filtrate is rendered alkaline with concentrated ammonia, while cooling with ice, whereby the zinc salts dissolve. Extracting thrice with methylene chloride/isopropanol (7:3) yields, after evaporating to dryness, a crude product which in accordance with the thin layer chromatogram contains 85 to 90% of 13-bromo-9,10-dihydrolysergic acid methyl ester. Chromatographical puridication on silica gel yields a pure product having a M.P. of 190° (decomp., high vacuum), $[\alpha]_D^{20} = -15.3°$ (c = 0.457 in methanol) and $[\alpha]_D^{20} = -16.4°$ (c = 0.432 in methylene chloride).

c. 13-bromo-9,10-dihydro-lysergic acid 5.5 g (15 millimols) of 13-bromo-9,10-dihydro-lysergic acid methyl ester are dissolved in 100 cc of methanol and 10 cc of methylene chloride, 40 cc of 1N caustic soda solution are added and stirring is effected at room temperature for 5 hours. Methylene chloride and methanol are removed by evaporation, the residue is diluted with a small amount of water and the pH is adjusted to 4.6 with glacial acetic acid. The resulting crystalline precipitate is filtered, washed with methanol and subsequently recrystallized from methanol which has been saturated with ammonia. The title compound is obtained in the form of colourless crystals having a M.P. of 316° (decomp. in a high vacuum), $[\alpha]_D^{20} = -57°$ (c = 0.5 in pyridine).

What we claim is:

1. A compound of the formula,

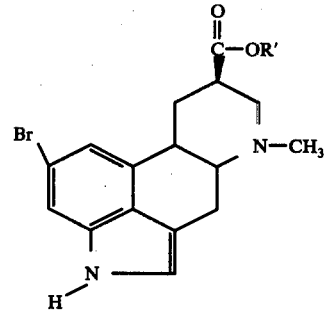

VIII wherein R' is alkyl of 1 to 6 carbon atoms or hydrogen.

2. A compound of claim 1, wherein R' is alkyl.
3. A compound of claim 1, wherein R' is methyl.
4. A compound of claim 1, wherein R' is hydrogen.
5. A compound of claim 1, which is 13-bromo-9,10-dihydrolysergic acid methyl ester.
6. A compound of claim 1, which is 13-bromo-9,10-dihydrolysergic acid.

* * * * *